United States Patent [19]
Clarkson, Jr. et al.

[11] Patent Number: 5,952,374
[45] Date of Patent: Sep. 14, 1999

[54] METHOD FOR INHIBITING THE DEVELOPMENT OF ALZHEIMER'S DISEASE AND RELATED DEMENTIAS- AND FOR PRESERVING COGNITIVE FUNCTION

[75] Inventors: Thomas Boston Clarkson, Jr.; Mary Susan Anthony, both of Clemmons; Yuanlong Pan, Winston-Salem; Michael R. Adams, Clemmons, all of N.C.; Doyle H. Waggle, St. Louis, Mo.

[73] Assignee: Protein Technologies International, Inc., St. Louis, Mo.

[21] Appl. No.: 08/939,691

[22] Filed: Sep. 29, 1997

[51] Int. Cl.$^6$ ............................................. A61K 31/35
[52] U.S. Cl. ........................................ 514/456; 514/457
[58] Field of Search ........................... 514/456, 457

[56] References Cited

U.S. PATENT DOCUMENTS

| | | | |
|---|---|---|---|
| 4,841,077 | 6/1989 | Ito et al. | 549/402 |
| 4,960,908 | 10/1990 | Ito et al. | 549/403 |
| 5,320,949 | 6/1994 | Shen | 435/68.1 |
| 5,352,384 | 10/1994 | Shen | 252/401 |
| 5,498,631 | 3/1996 | Gorbach et al. | 514/456 |
| 5,589,182 | 12/1996 | Tashiro et al. | 424/423 |
| 5,637,561 | 6/1997 | Shen et al. | 514/2 |
| 5,637,562 | 6/1997 | Shen et al. | 514/2 |
| 5,654,011 | 8/1997 | Jackson et al. | 424/195 |
| 5,733,926 | 3/1998 | Gorbach | 514/456 |

FOREIGN PATENT DOCUMENTS

| | | |
|---|---|---|
| 647408A1 | 4/1995 | European Pat. Off. . |
| 48008486 | 6/1970 | Japan . |
| 1258669 | 10/1989 | Japan . |
| WO9323069 | 11/1993 | WIPO . |
| WO9510530 | 4/1995 | WIPO . |
| WO9707811 | 3/1997 | WIPO . |

OTHER PUBLICATIONS

*The Flavanoids, Advances in Research Since 1980,* ed. J.B. Harbone, Chapman and Hall, Chapter 5, pp. 125–209 (1988).
Long–Term Potentiation in the Hippocampus is Blocked by Tyrosine Kinase Inhibitors, O'Dell, Kandel, and Grant, Nature, vol. 353, pp. 558–560 (Oct. 10, 1991).
*Inhibition of Tyrosine Phosphrylation Prevents Delayed Neutronal Death Following Cerebral Ischemia,* Kindy, J. Cereb. Blood Flow Metab., vol. 13, No. 3, pp. 372–377 (May 1993).
*A Review of the Clinical Effects of Phytoestrogens,* Knight and Eden, Obstetrics and Geynecology, vol. 87, No. 5, pp. 897–904 (May 1996).
Symposia: *Examining the Benefits of Dietary Phytoestrogens,* Inpharma, Dec. 6, 1996.
*Inhibition of Tyrosine Phosphorylation Attenuates Amino Acid Neurotransmitter Release From The Ischemic/Reperfused Rat Cerebral Cortex,* Phillis, Song, and O'Regan, Neurosci. Letter., vol. 207(3), pp. 151–154 (Apr. 5, 1996).
*Phospholipid Metabolism in Alzheimer's Disease and in a Human Cholinergic Cell,* Kanfer, Singh, Pettegrew, McCartney, and Sorrentino, J. of Lipid Mediators and Cell Signalling, vol. 14/1–3, pp. 361–363 (1996).
*Mechanism by which Ethanol Inhibits Phosphatidylcholine Biosynthesis in Human Leukemic Monocyte–Like U937 Cells,* Chu, Cell Biochem. and Function, vol. 12, No. 1, pp. 45–55 (Jan. 1994).
*Certain Plant Compounds Can Affect Women's Health,* Healthline, pp. 12–14 (Jun. 1992).
*Dose–Response Characteristics of Neonatal Exposure to Genistein on Pituitary Responsiveness to Gonadotropin Releasing Hormone and Volume of the Sexually Dimorphic Nucleus of the Preoptic Area SDN–POA in Postpubertal Castrated Female Rats,* Faber and Hughes, Reprod. Toxicol., vol. 7(1), pp. 35–39 (1993).
*The Effect of Neonatal Exposure to Diethylistilbesterol, Genistein, and Zearlenone on Pituitary Responsiveness and Sexually Dimorphic Nucleus Volume in the Castrated Adult Rat,* Faber Hughes, Biology of Reproduction, vol. 45(4), pp. 649–653 (1991).
*The Effect of Prenatal Exposure to the Phytoestrogen Genistein on Markers of* Sexual Differentiation in Rats, Levy, Faber, Ayyash, and Hughes, Toxicologist, vol. 13(1). p.188 (Mar. 1993).
*Commonly Occurring Plant Flavanoids Have Estrogenic Activity,* Miksicek, Miksicek, Molecular Pharmacology, vol. 44(1), pp. 37–43 (1993).
*Estrogenic Soybean Isoflavones and Chronic Disease: Risks and Benefits,* Clarkson, Anthony, and Hughes, Trends in Endocrinology and Metabolism, vol. 6(1), pp. 11–16 (1995).
*A Review of Phytoestrogens and Their Effect in Relation to Menopausal Symptoms,* Knight et al., Australian J. of Nut. and Dietetics, 53:1, pp. 5–11 (1996).

*Primary Examiner*—Theodore J. Criares
*Attorney, Agent, or Firm*—Richard B. Taylor

[57] ABSTRACT

Methods for inhibiting the development and relieving the symptoms of Alzheimer's disease and related dementias are provided. A phytoestrogenic isoflavone compound is administered to a human predisposed to developing Alzheimer's disease or a related dementia, or having Alzheimer's disease or a related dementia, in an amount effective to inhibit the development or relieve the symptoms of the disease. The phytoestrogenic isoflavone compound is selected from at least one of genistein, genistin, 6'-OMal genistin, 6'-OAc genistin, daidzein, daidzin, 6'-OMal daidzin, 6'-OAc daidzin, glycitein, glycitin, 6'-OMal glycitin, or mixtures thereof. The phytoestrogenic isoflavone compound is effective to up-regulate choline acetyltransferase mRNA and nerve growth factor mRNA.

90 Claims, No Drawings

METHOD FOR INHIBITING THE DEVELOPMENT OF ALZHEIMER'S DISEASE AND RELATED DEMENTIAS- AND FOR PRESERVING COGNITIVE FUNCTION

BACKGROUND OF THE INVENTION

The present invention relates to the discovery that phytoestrogen compounds are useful for up-regulating choline acetyltransferase mRNA and nerve growth factor mRNA in the brain, and therefore are useful for inhibiting the development of Alzheimer's disease and related dementias.

Alzheimer's disease and related dementias cause marked loss in cognitive function, often reducing an afflicted person to an invalid state. No cure is known for Alzheimer's and related dementias, and the causes of these diseases are not well understood.

Alzheimer's disease, however, is strongly associated with decreased choline acetyltransferase activity and the loss of cholinergic neurons. *Neurochemical Studies of Early-Onset Alzheimer's Disease: Possible Influence on Treatment,* Francis et al., *Lancet,* Vol. 4, pp. 7–11 (1985); *Alzheimer's Disease: A Cell Biological Perspective,* Kosik, *Science,* Vol. 256, pp. 780–83 (1992), both incorporated herein by reference. Cholinergic neurons appear to be essential for learning and memory processes, and choline acetyltransferase (hereinafter "ChAT") activity and nerve growth factor (hereinafter "NGF") are important for the function of cholinergic neurons. *Ovarian Steroid Deprivation Results in a Reversible Learning Impairment and Compromised Cholinergic Function in Female Sprague-Dawley Rats,* Singh et al., *Brain Research,* Vol. 644, pp. 305–12 (1994); *Effects of Estrogen Replacement on the Relative Levels of Choline Acetyltransferase, trkA, and Nerve Growth Factor Messenger RNAs in the Basal Forebrain and Hippocampal Formation of Adult Rats,* Gibbs et al., *Experimental Neurol.,* Vol. 129, pp. 70–80 (1994), both incorporated herein by reference.

Postmenopausal estrogen treatment has been shown to reduce the incidence of Alzheimer's disease and related dementias, to relieve symptoms of Alzheimer's disease, and to preserve cognitive function in women. *Estrogenic Effects on Memory in Women,* Sherwin, B., *Ann. N.Y. Acad. Sci.,* 743, pp. 213–31 (1994); *Oestrogen Replacement Therapy and Alzheimer's Disease,* Paganini-Hill, A., *Brit. J. Obstet. & Gynaecol.,* 103, pp. 80–86 (1996), both incorporated herein by reference. One mechanism by which supplemental estrogen may provide these beneficial effects is by increasing ChAT, ChAT activity, and NGF messenger RNA. Gibbs et al., *Experimental Neurol.* (above), Singh et al., *Brain Research* (above), and *Overiectomy Reduces ChAT Activity and NGF mRNA Levels in the Frontal Cortex and Hippocampus of the Female Sprague-Dawley Rat,* Singh et al., *Abstr. Soc. Neurosci.,* Vol. 19, p. 1254 (1993), incorporated herein by reference. Unfortunately, commonly used estrogens can significantly increase the risk of breast and uterine cancers in women, and have intolerable side effects for men and some women.

It is desirable, therefore, to find compounds like estrogen which can maintain normal levels of ChAT and NGF in cholinergic neurons in basal forebrain (such as septum) and their target brain tissues (cerebral cortex and hippocampus) to reduce or prevent loss of cholinergic neurons to prevent or delay the onset on Alzheimer's disease and related dementias, or to relieve the symptoms of Alzheimer's disease and related dementias.

Phytoestrogens are compounds that are structurally similar to estrogens which are derived from plants such as legumes, clovers, kudzu root (pueraria lobata), and oilseeds such as rapeseed. Phytoestrogens—particularly the isoflavones derived from soy and clover such as genistein, daidzein, glycitein, and their glucosidic derivatives—exhibit estrogenic properties in some mammalian and human tissues, and exhibit anti-estrogenic properties in other tissues by competitively inhibiting estrogen binding at estrogen receptor sites. Certain phytoestrogens, particularly genistein, are also known to have tyrosine kinase inhibitory activity. Unlike estrogen, however, these isoflavone phytoestrogens are not associated with an increased risk of cancer, and may actually inhibit the development of breast and uterine cancers.

SUMMARY OF THE INVENTION

A method of inhibiting the development of Alzheimer's disease and related dementias in a human is provided. A phytoestrogen compound selected from at least one of the isoflavone compounds genistein, 6-O-malonyl genistin (hereinafter "6'-OMal genistin"), 6-O-acetyl genistin (hereinafter "6-OAc genistin"), genistin, daidzein, 6-O-malonyl daidzin (hereinafter 6'-OMal daidzin"), 6'-O-acetyl daidzin (hereinafter "6'-OAc daidzin"), daidzin, glycitein, 6'O-malonyl glycitin (hereinafter "6'-OMal glycitin"), glycitin, or a mixture thereof, is administered to a human predisposed to developing Alzheimer's disease or a related dementia in an amount effective to inhibit the development of Alzheimer's disease or related dementia.

In another aspect, the invention is a method of aiding the preservation of cognitive function in a human predisposed to loss of cognitive function. A phytoestrogen compound selected from genistein, 6-OMal genistin, 6-OAc genistin, genistin, daidzein, 6-OMal daidzin, 6-OAc daidzin, daidzin, glycitein, glycitin, 6-OMal glycitin, or a mixture thereof is administered to a human in an amount effective to aid in the preservation of the cognitive function of said human.

In still another aspect, the invention is a method of up-regulating choline acetyltransferase mRNA in the brain of a human having, or predisposed to having, decreased choline acetyltransferase activity in the brain, or loss of cholinergic neurons. A phytoestrogen compound selected from genistein, 6-OMal genistin, 6-OAc genistin, genistin, daidzein, 6-OMal daidzin, 6-OAc daidzin, daidzin, glycitein, glycitin, 6-OMal glycitin, or a mixture thereof, is administered to a human having, or predisposed to having, decreased choline acetyltransferase activity in the brain, or loss of cholinergic neurons, in an amount effective to up-regulate choline acetyltransferase mRNA in the brain of the human.

In a further aspect, the invention is a method of up-regulating nerve growth factor mRNA in a human. A phytoestrogen compound selected from at least one of the isoflavone compounds genistein, 6-OMal genistin, 6-OAc genistin, genistin, daidzein, 6-OMal daidzin, 6-OAc daidzin, daidzin, glycitein, glycitin, 6-OMal glycitin, or a mixture thereof, is administered to a human in an amount effective to up-regulate nerve growth factor in the brain of said human.

In a final aspect, the present invention is a method of relieving the symptoms of Alzheimer's disease and related dementias. A phytoestrogen compound selected from at least one of the isoflavone compounds genistein, 6-OMal genistin, 6-OAc genistin, genistin, daidzein, 6-OMal daidzin, 6-OAc daidzin, daidzin, glycitein, 6-OMal glycitin, glycitin, or mixtures thereof, is administered to a human in an amount effective to relieve the symptoms of Alzheimer's disease or related dementia in the human.

DESCRIPTION OF THE PREFERRED EMBODIMENTS

The present invention resides in the discovery that the phytoestrogenic isoflavone compounds which may be derived from soy—genistein, 6-OMal genistin, 6-OAc genistin, genistin, daidzein, 6-OMal daidzin, 6-OAc daidzin, daidzin, glycitein, 6-OMal glycitin, glycitin, shown in Formulas 1 and 2 below—are useful in up-regulating choline acetyltransferase mRNA and neurotrophic factors such as brain derived neurotrophic factor ("BNDF") and nerve growth factor ("NGF") mRNA in the brain, and, therefore, are useful for inhibiting the development and relieving the symptoms of Alzheimer's disease and related dementias, and for aiding the preservation of cognitive function.

Formula 1

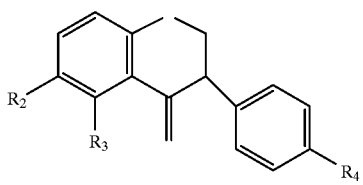

| Compound | $R_1$ | $R_2$ | $R_3$ | $R_4$ |
|---|---|---|---|---|
| Genistein | OH | H | OH | OH |
| Daidzein | OH | H | H | OH |
| Glycitein | OH | $OCH_3$ | H | OH |

Formula 2

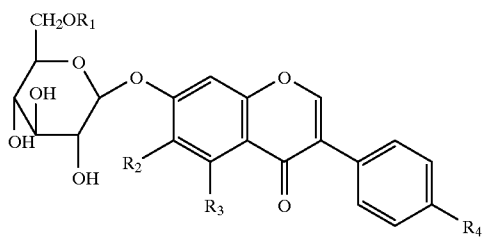

| Compound | $R_1$ | $R_2$ | $R_3$ | $R_4$ |
|---|---|---|---|---|
| Genistin | H | H | OH | OH |
| 6'-OMal genistin | $COCH_2CO_2H$ | H | OH | OH |
| 6'-OAc genistin | $COCH_3$ | H | OH | OH |
| Daidzin | H | H | H | OH |
| 6'-OMal daidzin | $COCH_2CO_2H$ | H | H | OH |
| 6'-OAc daidzin | $COCH_3$ | H | H | OH |
| Glycitin | H | $OCH_3$ | H | OH |
| 6'-OMal glycitin | $COCH_3$ | $OCH_3$ | H | OH |

As used herein "inhibit" is used in accordance with its generally accepted meaning and includes slowing, restraining, or impeding the progression, development, severity, or symptoms of Alzheimer's disease and related dementias. The term "up-regulate" is also used in accordance with its generally accepted meaning and includes increasing the translational activity, or the concentrations of the up-regulated mRNA to increase the concentrations or total amounts of the moiety produced by the up-regulated mRNA. The term "mRNA" is used in its conventional sense and means messenger ribonucleic acid.

The phytoestrogenic isoflavone compounds of Formulas 1 and 2 are naturally occurring substances which may be found in plants such as legumes, clover, and the root of the kudzu vine (pueraria root). Common legume sources of these phytoestrogenic isoflavone compounds include soy beans, chick peas, and various other types of beans and peas. Clover sources of these phytoestrogenic isoflavone compounds include red clover and subterranean clover. Soy beans are a particularly preferred source of the phytoestrogenic isoflavone compounds.

The phytoestrogenic isoflavone compounds of Formulas 1 and 2 may be isolated from the plant sources in which they naturally occur, and several may be synthetically prepared by processes known in the art. For example, daidzein may be isolated from red clover as disclosed by Wong (*J. Sci. Food Agr.*, Vol. 13, p. 304 (1962)) or may be isolated from the mold *Micromonospora halophytica* as provided by Ganguly and Sarre (*Chem. & Ind.* (London), p. 201 (1970)), both references of which are incorporated by reference herein. Daidzein may be synthetically prepared by the methods provided by Baker et al (*J. Chem. Soc.*, p. 274 (1933)), Wesley et al. (*Ber.* Vol. 66, p. 685 (1933)), Mahal et al. (*J. Chem. Soc.*, p. 1769 (1934)), Baker et al. (*J. Chem. Soc.*, p. 1852 (1953)), or Farkas (*Ber.* Vol. 90, p. 2940 (1957)), each reference of which is incorporated herein by reference. Daidzin may be synthetically prepared by the method of Farkas et al. (*Ber.*, Vol. 92, p. 819 (1959)), incorporated herein by reference. The daidzein isoflavone conjugates 6'-OMal daidzin and 6'-OAc daidzin can be prepared by a conventional saponification of daidzin with a malonyl or an acetyl anhydride, respectively.

Genistein may be synthetically prepared by the methods provided by Baker et al (*J. Chem. Soc.*, p. 3115 (1928)); Narasimhachari et al. (*J. Sci. Ind. Res.*, Vol. 12, p. 287 (1953)); Yoder et al., (*Proc. Iowa Acad. Sci.*, Vol. 61, p. 271 (1954); and Zemplen et al. (*Acta. Chim. Acad. Sci. Hung.*, Vol. 19, p. 277 (1959)), each reference of which is incorporated herein by reference. Genistin may be synthetically prepared by the method of Zemplen et al. (*Ber.*, Vol 76B, p. 1110 (1943)), incorporated herein by reference. The isoflavone conjugates of genistein 6'-OMal genistein and 6'-OAc genistein can be prepared by a conventional saponification of genistin with a malonyl or an acetyl anhydride, respectively.

A preferred method of isolating the phytoestrogenic isoflavone compounds of Formulas 1 and 2 from plant materials in which they naturally occur is to extract the plant materials with an alcohol, preferably methanol or ethanol, or an aqueous solution, preferably an aqueous alkaline solution, to remove the isoflavones from the plant material. It is preferred to comminute the plant material before extracting the phytoestrogenic isoflavone compounds to maximize recovery of the isoflavone compounds from the plant material. The phytoestrogenic isoflavone compounds can be isolated from the extract by conventional separation procedures such as reverse phase high performance liquid chromatography ("HPLC").

In a preferred embodiment, the phytoestrogenic isoflavone compounds genistein, genistin, 6'-OMal genistin, 6'-OAc genistin, daidzein, daidzin, 6'-OMal daidzin, 6'-OAc daidzin, glycitein, glycitin, and 6'-OMal glycitin are isolated from a soy material, preferably a commercially available soy material. Soy materials from which the phytoestrogenic isoflavone compounds can be isolated include: soy beans, dehulled soy beans, soy meal, soy flour, soy grits, soy flakes (full fat and defatted), soy cotyldeons, soy molasses, soy protein concentrate, soy whey, soy whey protein, and soy protein isolate. In one embodiment, the phytoestrogenic isoflavones are extracted from soy beans, dehulled soy beans, soy meal, soy flour, soy grits, soy flakes, soy protein concentrate, soy whey protein, or soy protein isolate, preferably soy meal, soy flour, soy grits, or soy flakes, with a low molecular weight organic extractant, preferably an alcohol, ethyl acetate, acetone, or ether, and most preferably aqueous ethyl alcohol or methyl alcohol. Most preferably the extractant has a pH of about the isoelectric point of soy protein (about pH 4 to pH 5) to minimize the amount of soy protein extracted by the extractant.

The extractant containing the phytoestrogenic isoflavones is separated from the insoluble soy materials to form an phytoestrogenic isoflavone enriched extract. If desired, a phytoestrogenic isoflavone enriched material may be recovered by concentrating the extract to remove the solvent and to produce a solid phytoestrogenic isoflavone enriched material.

In a more preferred embodiment the phytoestrogenic isoflavone compounds are further purified from other soy materials soluble in the extract by contacting the extract with a material which adsorbs the phytoestrogenic isoflavones in the extract, and eluting the adsorbed phytoestrogenic isoflavones out of the adsorbent material with a solvent which causes the isoflavones to be differentially eluted from the adsorbent material.

In a preferred embodiment, the phytoestrogenic isoflavones are separated from impurities in the extract by a conventional reverse phase HPLC separation. After extracting the isoflavones from the soy material and separation of the extract from the insoluble soy materials, the extract is filtered to remove insoluble materials that could plug an HPLC column. An HPLC column is prepared by packing a conventional commercially available HPLC column with a particulate adsorbent material which will releasably bind the isoflavones and impurities in the extract in a compound specific manner. The adsorbent material may be any reverse phase HPLC packing material, however, a preferred packing material may be chosen by the criteria of load capacity, separation effectiveness, and cost. One such preferred packing material is Kromasil C18 16 μm 100 Å beads available from Eka Nobel, Nobel Industries, Sweden.

The filtered extract is passed through the packed HPLC column until all the binding sites of the column are fully saturated with isoflavones, which is detected by the appearance of isoflavones in the effluent from the column. The HPLC column may then be eluted with a solvent to effect the separation. In a preferred embodiment, the eluent is a polar solvent such as ethanol, methanol, ethyl acetate, or acetonitrile, and preferably is an aqueous alcohol having an alcohol content of between about 30% and about 90%, most preferably about 50%, and most preferably the alcohol is ethanol.

The phytoestrogenic isoflavone compounds and impurities are separately collected from the column effluent. The isoflavone fractions of the eluent may be identified from other eluent fractions in accordance with conventional HPLC and analytical chemistry techniques. In a preferred embodiment the eluent fractions containing the phytoestrogenic aglucone isoflavones genistein, glycitein, and daidzein are collected separately since the aglucone isoflavones are believed to be particularly active in the up-regulation of ChAT and NGF mRNA, the inhibition and treatment of symptoms of Alzheimer's disease and related dementias, and in aiding in the preservation of cognitive function. Of the aglucone isoflavone materials, the fraction of effluent containing daidzein elutes from the column first, followed by a glycitein fraction, followed by the more polar genistein.

The isoflavone fractions of the eluent may be collected from the column, and the volatile content of the solvent (e.g. alcohol) can be removed by evaporation. The phytoestrogenic isoflavone compounds can be recovered directly if the all of the solvent is removed by evaporation, or may be recovered by chilling the remaining solvent (e.g. water) and centrifuging or filtering the remaining solvent.

In a particularly preferred embodiment the soy phytoestrogenic isoflavone conjugates—6'-OMal genistin, 6'-OAc genistin, 6'-OMal daidzin, 6'-OAc daidzin, and 6'-OMal glycitin—and the soy phytoestrogenic isoflavone glucosides—genistin, daidzin, and glycitin—are converted to their respective phytoestrogenic aglucone isoflavone forms—genistein, daidzein, and glycitein. The conversion of the isoflavone conjugates and isoflavone glucosides to the aglucone isoflavones can be effected in the soy substrate from which the phytoestrogenic isoflavones are to be extracted prior to the extraction, or may be effected in the isoflavone enriched extract after separation of the extract from the insoluble soy materials. As noted above, the aglucone isoflavone compounds are believed to be particularly active in the up-regulation of ChAT and NGF mRNA, the inhibition and treatment of symptoms of Alzheimer's disease and related dementias, and in aiding in the preservation of cognitive function, and the aglucone isoflavones are more easily separated from an extract containing water than their respective conjugate and glucoside forms since the aglucones are less water soluble.

The isoflavone conjugates 6'-OMal genistin, 6"-OAc genistin, 6'-OMal daidzin, 6'-OAc daidzin, and 6'-OMal glycitin can be converted to their respective glucosides genistin, daidzin, and glycitin by forming an aqueous alkaline solution of the soy substrate containing the isoflavones having a pH of about 6 to about 13, preferably about pH 9 to about pH 11, and treating the aqueous alkaline solution at a temperature of about 2° C. to about 121° C., preferably about 25° C. to about 75° C., for a period of time sufficient to effect the conversion, preferably about 30 minutes to about 5 hours, more preferably about 30 minutes to about 1.5 hours. The isoflavone glucosides genistin, daidzin, and glycitin can be converted to their respective aglucone forms genistein, daidzein, and glycitein by contacting the isoflavone glucosides with an enzyme capable of cleaving a 1,4-β-glucoside bond—preferably a commercially available alpha- or beta-galactosidase enzyme, a pectinase enzyme, a lactase enzyme, or a gluco-amylase enzyme—at a pH at which the enzyme is active, typically from about pH 3 to about pH 9, and at a temperature of about 25° C. to about 75° C., more preferably about 45° C. to about 65° C., for a period of time sufficient to effect the conversion, typically about 1 hour to about 24 hours, preferably about 1 hour to about 3 hours.

The phytoestrogenic aglucone isoflavones can be separated from the soy substrate using conventional separation procedures. For example, the aglucone isoflavones may be extracted from the soy substrate with a low molecular weight alcohol. The aglucone isoflavones may be separated from the extract by conventional recrystallization processes, or by HPLC. In a particularly preferred embodiment, an isoflavone composition isolated from a soy substrate for formulation into a pharmaceutical composition or a dietary supplement for use in the method of the present invention includes at least 40% genistein, at least 15% daidzein, and at least 1% glycitein. In another particularly preferred embodiment of the invention, an isoflavone composition isolated from a soy substrate for formulation into a pharmaceutical composition or a dietary supplement for use in the method of the present invention contains at least 85% genistein, at least 5% daidzein, and at least 0.5% glycitein.

Several of the isoflavone compounds of Formula 1 and Formula 2 are commercially available, and may be purchased for formulation into pharmaceutical compositions or dietary supplements useful in the method of the present invention. For example, genistein, daidzein, and glycitein are commercially available and may be purchased, for example, from Indofine Chemical Company Inc., P.O. Box 473, Somerville, N.J. 08876.

The phytoestrogenic isoflavone compounds of Formulas 1 and 2 may be administered to a human in a pharmaceutical formulation to inhibit the development or relieve the symptoms of Alzheimer's disease or related dementias, to aid in the preservation of cognitive function, or to up-regulate ChAT and NGF mRNA in the brain of the human. Pharmaceutical formulations incorporating the isoflavone compounds obtained by any of the methods above, or purchased from a commercial source, can be prepared by procedures known in the art. For example, the isoflavone compounds can be formulated into tablets, capsules, powders, suppositories, suspensions, solutions for parenteral administration including intravenous, intramuscular, and subcutaneous administration, and into solutions for application onto patches for transdermal application with common and conventional carriers, binders, diluents, and excipients. In a preferred embodiment, a pharmaceutical formulation for use in the methods of the present invention includes a phytoestrogenic isoflavone material containing at least 40% genistein, at least 15% daidzein, and at least 1% glycitein. In another preferred embodiment, a pharmaceutical formulation includes an isoflavone material containing at least 85% genistein, at least 5% daidzein, and at least 0.5% glycitein.

Inert pharmaceutically acceptable carriers useful to form pharmaceutical formulations in accordance with the present invention include starch, mannitol, calcium sulfate, dicalcium phosphate, magnesium stearate, silicic derivatives, and/or sugars such as sucrose, lactose, and glucose. Binding agents include carboxymethyl cellulose and other cellulose derivatives, gelatin, natural and synthetic gums including alginates such as sodium alginate, polyethylene glycol, waxes and the like. Diluents useful in the invention include a suitable oil, saline, sugar solutions such as aqueous dextrose or aqueous glucose, and glycols such as polyethylene or polypropylene glycol. Other excipients include lubricants such as sodium oleate, sodium acetate, sodium stearate, sodium chloride, sodium benzoate, talc, and magnesium stearate, and the like; disintegrating agents including agar, calcium carbonate, sodium bicarbonate, starch, xanthan gum, and the like; and adsorptive carriers such as bentonite and kaolin. Coloring and flavoring agents may also be added to the pharmaceutical formulations.

Dietary supplements incorporating the phytoestrogenic isoflavone compounds of Formulas 1 and/or 2 can be prepared by adding the isoflavone compounds to a food in the process of preparing the food, independent of the plant or protein material from which the isoflavone compounds are derived. The foods to which the isoflavone compounds may be added include almost all foods. For example, the isoflavone compounds can be added to foods including, but not limited to, meats such as ground meats, emulsified meats, marinated meats, and meats injected with the isoflavone compounds; beverages such as nutritional beverages, sports beverages, protein fortified beverages, juices, milk, milk alternatives, and weight loss beverages; cheeses such as hard and soft cheeses, cream cheese, and cottage cheese; frozen desserts such as ice cream, ice milk, low fat frozen desserts, and non-dairy frozen desserts; yogurts; soups; puddings; bakery products; salad dressings; and dips and spreads such as mayonnaise and chip dips. The isoflavone compounds are added to the food in an amount selected to deliver a desired dose of the isoflavone compounds to the consumer of the food. In a preferred embodiment, a phytoestrogenic isoflavone material added to a food for use as a dietary supplement in accordance with the methods of the present invention contains at least 40% genistein, at least 15% daidzein, and at least 1% glycitein. In another preferred embodiment, a phytoestrogenic isoflavone material added to a food contains at least 85% genistein, at least 5% daidzein, and at least 0.5% glycitein.

The phytoestrogenic isoflavone compounds of Formulas 1 and/or 2 may also be administered in a phytoestrogenic isoflavone enriched soy protein material incorporated into a dietary supplement formulation for inhibiting the development or relieving the symptoms of Alzheimer's disease or related dementias, aiding in the preservation of cognitive function, or up-regulating ChAT and NGF mRNA in the brain. In a preferred method of forming the isoflavone rich soy protein material, a phytoestrogenic isoflavone enriched soy protein isolate is formed. A commercially available defatted soy flake material is extracted with an aqueous alkaline solution, typically a calcium hydroxide or a sodium hydroxide solution having a pH of about 7.5 to about 10, to form an extract containing the isoflavones, protein, and other water soluble components of the soy flake material. The extract is then treated with an acid to lower the pH of the extract to about the isoelectric point of the protein, preferably to a pH of about 4 to about 5, and most preferably to a pH of about 4.4 to about 4.6, thereby precipitating a protein curd which captures significant amounts of the isoflavones. Preferably the conjugate and glucoside isoflavones are converted to aglucone isoflavones in the extract, as described above, to increase the amount of isoflavones captured in the protein curd, and to provide the benefits of the aglucone isoflavones. The protein curd is then separated from the extract, preferably by centrifugation, and dried to form the protein isolate. Preferably, unlike conventional processes to produce a protein isolate, the curd is not washed with water or is washed with a minimal amount of water to minimize the loss of the isoflavones from the protein isolate.

Other phytoestrogenic isoflavone enriched soy protein materials include soy protein concentrates and soy whey protein materials which include significant amounts of the isoflavones of Formulas 1 and/or 2.

The phytoestrogenic isoflavone compound can be administered to: a human predisposed to developing Alzheimer's disease or a related dementia for the purpose of inhibiting the disease; a human predisposed to loss of cognitive function for the purpose of aiding in the preservation of cognitive function; a human suffering Alzheimer's disease or a related dementia, particularly someone having decreased ChAT activity or concentrations of ChAT in the brain, or decreased cholinergic neuron activity or concentrations in the brain, for the purpose of relieving the symptoms of the disease; to a human having decreased, or predisposed to having decreased, ChAT activity, or concentrations of ChAT in the brain for the purpose of increasing ChAT activity in the brain; to a human having decreased, or predisposed to having decreased, cholinergic neuron activity or concentrations of cholinergic neurons in the brain for the purpose of increasing cholingeric neuron activity or concentration of cholinergic neurons in the brain; or to a human requiring up-regulation of NGF mRNA in the brain. Typically the phytoestrogenic compound should be administered to persons most likely to develop Alzheimer's disease or a related dementia, such as persons genetically predisposed to such diseases, or persons over 45 years of age. In a particularly preferred embodiment of the invention, the phytoestrogenic isoflavone compound is administered to a perimenopausal or postmenopausal woman.

The particular dosage of the phytoestrogenic isoflavone compound to be administered to a human predisposed to developing Alzheimer's disease or a related dementia for the inhibition of the development of the disease will depend on the route of administration, and other risk factors for developing Alzheimer's disease or the related dementia. The dosage of the phytoestrogenic isoflavone compound to be administered to a human predisposed to a loss of cognitive function for the purpose of aiding in preservation of cognitive function also will depend on the route of administration, and the risk factors predisposing the human to loss of cognitive function. The dosage of the phytoestrogenic isoflavone compound to be administered to a human having decreased, or predisposed to having decreased, ChAT activity in the brain or loss of cholinergic neurons will depend on the route of administration and the degree of loss, or predisposition to loss, of ChAT activity in the brain or degree of loss, or predisposition to loss, of cholinergic neurons or cholinergic neuron activity. The dosage of the phytoestrogenic isoflavone compound to be administered to a human to up-regulate NGF mRNA will depend on the route of administration and the degree of up-regulation of the NGF mRNA desired.

The dosage of the phytoestrogenic isoflavone compound to be administered to a human having Alzheimer's disease or a related dementia to relieve the symptoms of the disease will depend on the route of administration, the extent of the disease, and other risk factors. The dosage can be related to the degree that the human suffering the disease has decreased ChAT activity in the brain so the phytoestrogen isoflavone compound can be administered in an amount required to increase ChAT activity in the brain, preferably to normal levels. The dosage may also be related to the degree that the human suffering the disease has suffered a loss of cholinergic neurons, or cholinergic neuron activity, so the phytoestrogenic isoflavone compound can be administered in an amount required to increase the amount of cholinergic neurons, or cholinergic neural activity, preferably to normal levels.

Generally acceptable and effective daily doses of the phytoestrogenic isoflavone compound for the above applications may be from about 10 mg/day to about 1000 mg/day. Preferably the daily dose of the phytoestrogenic isoflavone compound in the method of the present invention is about 20 mg/day to about 500 mg/day, more preferably from about 30 mg/day to about 300 mg/day, and most preferably from about 50 mg/day to about 150 mg/day.

The phytoestrogenic isoflavone compound should be administered in an amount effective to increase the concentration of the isoflavones and/or their metabolites in the blood or urine of the human to whom the compound is administered. Preferably, the phytoestrogenic isoflavone compound is administered in an amount effective to increase the concentration of at least one of daidzein, equol, o-desmethylangolensin, dihydrodaidzein, genistein, dihydrogenistein and 6-hydroxy-o-desmethylangolensin in the blood or urine of the human to whom the compound is administered. Dihydrodaidzein, equol, and o-desmethylangolensin are metabolites produced by the human body in catabolism of daidzein, and dihydrogenistein and 6'-hydroxy-o-desmethylangolensin are metabolites produced by the human body in the catabolism of genistein. See A Urinary Profile Study of Dietary Phytoestrogens. The Identification and Mode of Metabolism of New Isoflavanoids., Joannou et al., J. Steroid Biochem. Molec. Biol., Vol. 54, No. 3/4, pp. 167–84 (1995), incorporated herein by reference, including the structures of dihydrodaidzein, equol, o-desmethylangolensin, dihydrogenistein, and 6'-hydroxy-o-desmethylangolensin.

The following non-limiting formulations illustrate pharmaceutical and dietary formulations including the phytoestrogenic isoflavone compounds of Formulas 1 and/or 2 which may be used in accordance with the methods of the present invention.

FORMULATIONS

The following Formulations 1–4 illustrate pharmaceutical formulations including a phytoestrogenic isoflavone compound of Formula 1 and/or Formula 2. In the formulations, "Active ingredient" means an isoflavone compound or a mixture of isoflavone compounds of Formulas 1 and/or 2.

Formulation 1

Gelatin Capsules

Hard gelatin capsules are prepared using the following ingredients: Active ingredient 0.1–1000 mg/capsule; Starch, NF 0–600 mg/capsule; Starch flowable powder 0–600 mg/capsule; Silicone fluid 350 centistokes 0–20 mg/capsule. The ingredients are mixed, passed through a sieve, and filled into capsules.

Formulation 2

Tablets

Tablets are prepared using the following ingredients: Active ingredient 0.1–1000 mg/tablet; Microcrystalline cellulose 20–300 mg/tablet; Starch 0–50 mg/tablet; Magnesium stearate or stearate acid 0–15 mg/tablet; Silicon dioxide, fumed 0–400 mg/tablet; silicon dioxide, colloidal 0–1 mg/tablet, and lactose 0–100 mg/tablet. The ingredients are blended and compressed to form tablets.

Formulation 3

Suspensions

Suspensions are prepared using the following ingredients: Active ingredient 0.1–1000 mg/5 ml; Sodium carboxymethyl cellulose 50–700 mg/5 ml; Sodium benzoate 0–10 mg/5 ml; Purified water 5 ml; and flavor and color agents as needed.

Formulation 4

Parenteral Solutions

A parenteral composition is prepared by stirring 1.5% by weight of active ingredient in 10% by volume propylene glycol and water. The solution is made isotonic with sodium chloride and sterilized.

The following Formulations 5–8 illustrate dietary supplements that may be formed using an isolated soy protein rich in several of the phytoestrogenic isoflavone compounds of Formula 1 and/or Formula 2. The isoflavone rich isolated soy protein in the following examples typically contains between about 1 to about 3 milligrams of the isoflavone compounds per gram of soy protein.

Formulation 5

Ready to Drink Beverage

A ready to drink beverage is formed of the following components:

| Ingredient | Percent of composition, by weight |
|---|---|
| Water | 80–85 |
| Isoflavone rich isolated soy protein | 10–15 |
| Sucrose | 5–8 |
| Cocoa | 0.1–1 |
| Vitamins/Minerals | 0.1–1 |
| Flavor | 0.1–1 |
| Cellulose gel | 0.1–0.5 |

The ready to drink beverage may be served in 8 ounce servings containing about 20 grams of isolated soy protein including about 20 to about 60 milligrams of the isoflavone compounds.

Formulation 6

Powdered Beverage

A powdered beverage is formed of the following components:

| Ingredient | Percent of composition, by weight |
|---|---|
| Isoflavone rich isolated soy protein | 85–90 |
| Sucrose | 8–15 |
| Maltodextrin | 1–5 |
| Vitamins/Minerals | 0.5–2 |
| Aspartame | 0–0.5 |
| Flavor | 0–0.5 |

30 grams of the powdered beverage formulation may be added to water to form a serving containing about 20 grams of isolated soy protein including about 20 to about 60 milligrams of the isoflavone compounds.

Formulation 7

Food Bar

A food bar is formed of the following components:

| Ingredients | Percent of composition, by weight |
|---|---|
| Isoflavone rich isolated soy protein | 20–30 |
| Corn syrup | 35–45 |
| Rice syrup solids | 7–14 |
| Glycerin | 1–5 |
| Cocoa | 2–7 |
| Compound coating | 15–25 |

The food bar may be served in 70 gram portions containing about 15 grams of soy protein having about 15 to about 45 milligrams of the isoflavone compounds therein.

Formulation 8

Soy Yogurt

A soy yogurt is formed of the following components:

| Ingredients | Percent of composition, by weight |
|---|---|
| Water | 65–75 |
| Isoflavone rich isolated soy protein | 5–15 |
| Sucrose | 3–8 |
| Corn starch | 1–5 |
| Dextrin | 0.3–1 |
| Cellulose gel | 1–3 |
| Culture (yogurt) | 0.01–0.1 |
| Fruit | 10–20 |
| Vitamins/Minerals | 0.05–0.3 |

The soy yogurt may be served in a 170 gram serving containing about 8 grams of soy protein having about 8 to about 24 milligrams of isoflavone compounds therein.

The following non-limiting test examples illustrate the methods of the present invention.

EXAMPLE 1

A study of the effect on ChAT and brain derived neurotrophic factor ("BDNF") mRNAs in the brain of retired female breeder rats of diets supplemented with phytoestrogenic isoflavones, 17-β estradiol (estrogen), and a control diet containing neither phytoestrogenic isoflavones or an estrogen-like compound is conducted.

Fifteen retired female breeder rats weighing 300 g to 360 g are housed in separate cages and are maintained on a 12 hour light/12 hour dark cycle, with access to food and water ad libitum. The rats are randomized into three groups of five based on body weight. The rats are ovariectiomized, and are fed a casein/lactalbumin-based control diet containing no estrogen-like substances for a period of three days after the surgery. Group 1 is then fed the control diet supplemented with soy phytoestrogen isoflavones equivalent to a human dose of 150 mg of total isoflavones per day for a period of 8 weeks. Group 2 is fed the control diet supplemented with 17-β estradiol ("E2") equivalent to a human dose of 2 mg per day for a period of 8 weeks. Group 3 is fed the control diet with no supplemental materials for the 8 week period of the experiment.

At the end of the eight week treatments the rats are euthanized with phenobarbital (100 mg/kg). Blood samples are collected by cardiac puncture at necropsy, and serum samples are used to determine estradiol and phytoestrogenic isoflavone levels. The brains are removed and processed to determine the effect on ChAT and BDNF mRNA in the hippocampus and in the frontal cortex.

The E2 and phytoestrogenic isoflavones are found to significantly up-regulate both ChAT and BDNF mRNA in the frontal cortex portion of the brain of the rats compared to the control.

EXAMPLE 2

A study of the effect on NGF mRNAs in the brain of young female rats of diets supplemented with phytoestrogenic isoflavones, 17-β estradiol ("E2"), and a control diet containing neither phytoestrogenic isoflavones or an estrogen-like compound is conducted.

Fifteen young adult female rats weighing 180 g to 250 g are housed in separate cages and are maintained on a 12 hour light/12 hour dark cycle, with access to food and water ad libitum. The rats are randomized into three groups of five based on body weight. The rats are ovariectiomized, and are fed a casein/lactalbumin-based control diet containing no estrogen-like substances for a period of three days after the surgery. Group 1 is then fed the control diet supplemented with soy phytoestrogen isoflavones equivalent to a human dose of 150 mg of total isoflavones per day for a period of 8 weeks. Group 2 is fed the control diet supplemented with 17-β estradiol ("E2") equivalent to a human dose of 2 mg per day for a period of 8 weeks. Group 3 is fed the control diet with no supplemental materials for the 8 week period of the experiment.

At the end of the eight week treatments the rats are euthanized with phenobarbital (100 mg/kg). Blood samples are collected by cardiac puncture at necropsy, and serum samples are used to determine estradiol and phytoestrogenic isoflavone levels. The brains are removed and processed to determine the effect on NGF mRNA in the hippocampus and in the frontal cortex.

The phytoestrogenic isoflavones are found to marginally up-regulate NGF mRNA in the hippocampus portion of the brain of the young rats relative to the control, and E2 is found to significantly up-regulate NGF mRNA in the hippocampus portion of the brain of the young rats.

EXAMPLE 3

Five to fifty men having mild to moderate Alzheimer's disease are selected for clinical study. The men are divided into two groups, one of which receives a soy protein dietary supplement containing between 30 mg to 500 mg per day of phytoestrogenic isoflavones, the other of which receives a soy protein dietary supplement from which the phytoestrogenic isoflavones have been removed by alcohol extraction. The diets of the two groups are selected to contain no further source of isoflavones, and no source of estrogen or androgen is administered to either of the two groups. The diets are continued for 6 to 12 months.

Prior to beginning the diets, the patients are benchmarked as to cognitive ability. The benchmarked symptoms are measured again for each group after the groups have been on the diets for the prescribed period of the study. Activity of the phytoestrogenic isoflavone compounds to aid in the preservation of cognitive function and to inhibit the development of Alzheimer's disease is shown by significant retention of cognitive function in the patients on the diet containing the phytoestrogenic isoflavone compounds relative to the patients on the diet containing no phytoestrogenic isoflavone compounds. Activity of the phytoestrogenic isoflavone compounds to relieve the symptoms of Alzheimer's disease is shown by improved cognitive function in the patients on the diet containing the phytoestrogenic isoflavone compounds relative to the cognitive function of the same patients at the start of the study.

EXAMPLE 4

Five to fifty perimenopausal or postmenopausal women having mild to moderate Alzheimer's disease are selected for clinical study. The women are divided into two groups, one of which receives a soy protein dietary supplement containing between 30 mg to 500 mg per day of phytoestrogenic isoflavones, the other of which receives a soy protein dietary supplement from which the phytoestrogenic isoflavones have been removed by alcohol extraction. The diets of the two groups are selected to contain no further source of isoflavones, and no source of estrogen or androgen is administered to either of the two groups. The diets are continued for 6 to 12 months.

Prior to beginning the diets, the patients are benchmarked as to cognitive ability. The benchmarked symptoms are measured again for each group after the groups have been on the diets for the prescribed period of the study. Activity of the phytoestrogenic isoflavone compounds to aid in the preservation of cognitive function and to inhibit the development of Alzheimer's disease is shown by significant retention of cognitive function in the patients on the diet containing the phytoestrogenic isoflavone compounds relative to the diet containing no phytoestrogenic isoflavone compounds. Activity of the phytoestrogenic isoflavone compounds to relieve the symptoms of Alzheimer's disease is shown by improved cognitive function in the patients on the diet containing the phytoestrogenic isoflavone compounds relative to the cognitive function of the same patients at the start of the study.

Utility of the phytoestrogenic isoflavone compounds of Formula 1 or 2 for: inhibiting the development of Alzheimer's disease or a related dementia in a human; relieving the symptoms of Alzheimer's disease or a related dementia in a human; aiding the preservation of cognitive function in a human; up-regulating ChAT mRNA in the brain of a human; or up-regulating NGF mRNA in the brain of a human is evidenced by activity in at least one of the above examples.

It is to be understood that the foregoing are merely preferred embodiments of the invention and that various changes and alterations can be made without departing from the spirit and broader aspects thereof as set forth in the appended claims, which are to be interpreted in accordance with the principles of patent law including the Doctrine of Equivalents.

What is claimed is:

1. A method of inhibiting the development of Alzheimer's disease and related dementias in a human, comprising:

administering to a human predisposed to developing Alzheimer's disease or a related dementia an amount of a phytoestrogenic isoflavone compound effective to inhibit the development of Alzheimer's disease or related dementia in said human, where said phytoestrogenic isoflavone compound is selected from at least one of genistein, 6-OMal genistin, 6-OAc genistin, genistin, daidzein, 6-OMal daidzin, 6-OAc daidzin, daidzin, glycitein, 6-OMal glycitin, glycitin, or mixtures thereof.

2. The method of claim 1 wherein said human is at least 45 years of age.

3. The method of claim 1 wherein said human administration of said phytoestrogenic isoflavone compound increases choline acetyltransferase activity in the brain of said human.

4. The method of claim 1 wherein administration of said phytoestrogenic isoflavone compound increases the amount of cholinergic neurons in the brain of said human.

5. The method of claim 1 wherein administration of said phytoestrogenic isoflavone is effective to up-regulate nerve growth factor mRNA in the brain of said human.

6. The method of claim 1 wherein said human is a postmenopausal woman.

7. The method of claim 1 wherein administration of said phytoestrogenic isoflavone compound is effective to increase the concentration of at least one of daidzein, equol, o-desmethylangolensin, dihydrodaidzein, genistein, and 6-hydroxy-o-desmethylangolensin in the blood of said human.

8. The method of claim 1 wherein between about 10 mg to about 1000 mg of said phytoestrogenic isoflavone compound is administered to said human per day.

9. The method of claim 8 wherein between about 20 mg to about 500 mg of said phytoestrogenic isoflavone compound is administered to said human per day.

10. The method of claim 9 wherein between about 30 mg to about 300 mg of said phytoestrogenic isoflavone compound is administered to said human per day.

11. The method of claim 10 wherein between about 50 mg to about 150 mg of said phytoestrogenic isoflavone compound is administered to said human per day.

12. The method of claim 1 wherein said phytoestrogenic isoflavone compound is administered to said human in a soy protein material dietary supplement.

13. The method of claim 12 wherein said soy protein material is a phytoestrogenic isoflavone enriched material.

14. The method of claim 12 wherein said soy protein material is enriched in at least one of the aglucone isoflavones genistein, daidzein, and glycitein.

15. The method of claim 12 wherein said phytoestrogenic isoflavone compound is administered to said human in a beverage containing said soy protein material.

16. The method of claim 12 wherein said phytoestrogenic isoflavone compound is administered to said human in a food bar containing said soy protein material.

17. The method of claim 12 wherein said phytoestrogenic isoflavone compound is administered to said human in a yogurt containing said soy protein material.

18. The method of claim 1 wherein said phytoestrogenic isoflavone compound is administered to said human in a pharmaceutical composition.

19. The method of claim 18 wherein said pharmaceutical composition is a pill or a capsule containing said phytoestrogenic isoflavone compound.

20. A method of aiding the preservation of cognitive function in a human predisposed to loss of cognitive function, comprising:
   administering to said human an amount of a phytoestrogenic isoflavone compound effective to aid in the preservation of the cognitive function of said human, where said phytoestrogenic isoflavone compound is selected from at least one of genistein, 6-OMal genistin, 6-OAc genistin, genistin, daidzein, 6-OMal daidzin, 6-OAc daidzin, daidzin, glycitein, 6-OMal glycitin, glycitin, or mixtures thereof.

21. The method of claim 20 wherein said human is at least 45 years of age.

22. The method of claim 20 wherein administration of said phytoestrogenic isoflavone compound increases choline acetyltransferase activity in the brain of said human.

23. The method of claim 20 wherein administration of said phytoestrogenic isoflavone compound increases the amount of cholinergic neurons in the brain of said human.

24. The method of claim 20 wherein administration of said phytoestrogenic isoflavone is effective to up-regulate nerve growth factor mRNA in the brain of said human.

25. The method of claim 20 wherein said human is a postmenopausal woman.

26. The method of claim 20 wherein administration of said phytoestrogenic isoflavone compound is effective to increase the concentration of at least one of daidzein, equol, o-desmethylangolensin, dihydrodaidzein, genistein, and 6-hydroxy-o-desmethylangolensin in the blood of said human.

27. The method of claim 20 wherein between about 10 mg to about 1000 mg of said phytoestrogenic isoflavone compound is administered to said human per day.

28. The method of claim 27 wherein between about 20 mg to about 500 mg of said phytoestrogenic isoflavone compound is administered to said human per day.

29. The method of claim 28 wherein between about 30 mg to about 300 mg of said phytoestrogenic isoflavone compound is administered to said human per day.

30. The method of claim 29 wherein between about 50 mg to about 150 mg of said phytoestrogenic isoflavone compound is administered to said human per day.

31. The method of claim 20 wherein said phytoestrogenic isoflavone compound is administered to said human in a soy protein material dietary supplement.

32. The method of claim 31 wherein said soy protein material is a phytoestrogenic isoflavone enriched material.

33. The method of claim 31 wherein said soy protein material is enriched in at least one of the aglucone isoflavones genistein, daidzein, and glycitein.

34. The method of claim 31 wherein said phytoestrogenic isoflavone compound is administered to said human in a beverage containing said soy protein material.

35. The method of claim 31 wherein said phytoestrogenic isoflavone compound is administered to said human in a food bar containing said soy protein material.

36. The method of claim 31 wherein said phytoestrogenic isoflavone compound is administered to said human in a yogurt containing said soy protein material.

37. The method of claim 20 wherein said phytoestrogenic isoflavone compound is administered to said human in a pharmaceutical composition.

38. The method of claim 37 wherein said pharmaceutical composition is a pill or a capsule containing said phytoestrogenic isoflavone compound.

39. A method of up-regulating choline acetyltransferase mRNA in the brain of a human having, or predisposed to having, decreased choline acetyltransferase activity in the brain or loss of cholinergic neurons, comprising:
   administering to said human an amount of a phytoestrogenic isoflavone compound effective to up-regulate choline acetyltransferase mRNA in the brain of said human, where said phytoestrogenic isoflavone compound is selected from at least one of genistein, 6-OMal genistin, 6-OAc genistin, genistin, daidzein, 6-OMal daidzin, 6-OAc daidzin, daidzin, glycitein, 6-OMal glycitin, glycitin, or mixtures thereof.

40. The method of claim 39 wherein said human is at least 45 years of age.

41. The method of claim 39 wherein administration of said phytoestrogenic isoflavone is effective to up-regulate nerve growth factor mRNA in the brain of said human.

42. The method of claim 39 wherein said human is a postmenopausal woman.

43. The method of claim 39 wherein administration of said phytoestrogenic isoflavone compound is effective to increase the concentration of at least one of daidzein, equol, o-desmethylangolensin, dihydrodaidzein, genistein, and 6-hydroxy-o-desmethylangolensin in the blood of said human.

44. The method of claim 39 wherein between about 10 mg to about 1000 mg of said phytoestrogenic isoflavone compound is administered to said human per day.

45. The method of claim 44 wherein between about 20 mg to about 500 mg of said phytoestrogenic isoflavone compound is administered to said human per day.

46. The method of claim 45 wherein between about 30 mg to about 300 mg of said phytoestrogenic isoflavone compound is administered to said human per day.

47. The method of claim 46 wherein between about 50 mg to about 150 mg of said phytoestrogenic isoflavone compound is administered to said human per day.

48. The method of claim 39 wherein said phytoestrogenic isoflavone compound is administered to said human in a soy protein material dietary supplement.

49. The method of claim 48 wherein said soy protein material is a phytoestrogenic isoflavone enriched material.

50. The method of claim 48 wherein said soy protein material is enriched in at least one of the aglucone isoflavones genistein, daidzein, and glycitein.

51. The method of claim 48 wherein said phytoestrogenic isoflavone compound is administered to said human in a beverage containing said soy protein material.

52. The method of claim 48 wherein said phytoestrogenic isoflavone compound is administered to said human in a food bar containing said soy protein material.

53. The method of claim 48 wherein said phytoestrogenic isoflavone compound is administered to said human in a yogurt containing said soy protein material.

54. The method of claim 39 wherein said phytoestrogenic isoflavone compound is administered to said human in a pharmaceutical composition.

55. The method of claim 54 wherein said pharmaceutical composition is a pill or a capsule containing said phytoestrogenic isoflavone compound and a pharmaceutical carrier.

56. A method of up-regulating nerve growth factor mRNA in a human, comprising:
 administering to said human an amount of a phytoestrogenic isoflavone compound effective to up-regulate nerve growth factor mRNA in the brain of said human, where said phytoestrogenic isoflavone compound is selected from at least one of genistein, 6-OMal genistin, 6-OAc genistin, genistin, daidzein, 6-OMal daidzin, 6-OAc daidzin, daidzin, glycitein, 6-OMal glycitin, glycitin, or mixtures thereof.

57. The method of claim 56 wherein said human is at least 45 years of age.

58. The method of claim 56 wherein said human is a postmenopausal woman.

59. The method of claim 56 wherein administration of said phytoestrogenic isoflavone compound increases the concentration of at least one of daidzein, equol, o-desmethylangolensin, dihydrodaidzein, genistein, and 6-hydroxy-o-desmethylangolensin in the blood of said human.

60. The method of claim 56 wherein between about 10 mg to about 1000 mg of said phytoestrogenic isoflavone compound is administered to said human per day.

61. The method of claim 60 wherein between about 20 mg to about 500 mg of said phytoestrogenic isoflavone compound is administered to said human per day.

62. The method of claim 61 wherein between about 30 mg to about 300 mg of said phytoestrogenic isoflavone compound is administered to said human per day.

63. The method of claim 62 wherein between about 50 mg to about 150 mg of said phytoestrogenic isoflavone compound is administered to said human per day.

64. The method of claim 56 wherein said phytoestrogenic isoflavone compound is administered to said human in a soy protein material dietary supplement.

65. The method of claim 64 wherein said soy protein material is a phytoestrogenic isoflavone enriched material.

66. The method of claim 64 wherein said soy protein material is enriched in at least one of the aglucone isoflavones genistein, daidzein, and glycitein.

67. The method of claim 64 wherein said phytoestrogenic isoflavone compound is administered to said human in a beverage containing said soy protein material.

68. The method of claim 64 wherein said phytoestrogenic isoflavone compound is administered to said human in a food bar containing said soy protein material.

69. The method of claim 64 wherein said phytoestrogenic isoflavone compound is administered to said human in a yogurt containing said soy protein material.

70. The method of claim 56 wherein said phytoestrogenic isoflavone compound is administered to said human in a pharmaceutical composition.

71. The method of claim 70 wherein said pharmaceutical composition is a pill or a capsule containing said phytoestrogenic isoflavone compound and a pharmaceutical carrier.

72. A method of relieving the symptoms of Alzheimer's disease and related dementias in a human, comprising:
 administering to a human having Alzheimer's disease or a related dementia an amount of a phytoestrogenic isoflavone compound effective to relieve the symptoms of Alzheimer's disease or related dementia in said human, where said phytoestrogenic isoflavone compound is selected from at least one of genistein, 6-OMal genistin, 6-OAc genistin, genistin, daidzein, 6-OMal daidzin, 6-OAc daidzin, daidzin, glycitein, 6-OMal glycitin, glycitin, or mixtures thereof.

73. The method of claim 72 wherein said human is at least 45 years of age.

74. The method of claim 72 wherein said human has decreased choline acetyltransferase activity in the brain, and administration of said phytoestrogenic isoflavone compound increases choline acetyltransferase activity in the brain of said human.

75. The method of claim 72 wherein said human has suffered a loss of cholinergic neurons and administration of said phytoestrogenic isoflavone compound increases the amount of cholinergic neurons in the brain of said human.

76. The method of claim 72 wherein administration of said phytoestrogenic isoflavone is effective to up-regulate nerve growth factor mRNA in the brain of said human.

77. The method of claim 72 wherein said human is a postmenopausal woman.

78. The method of claim 72 wherein administration of said phytoestrogenic isoflavone compound is effective to increase the concentration of at least one of daidzein, equol, o-desmethylangolensin, dihydrodaidzein, genistein, and 6-hydroxy-o-desmethylangolensin in the blood of said human.

79. The method of claim 72 wherein between about 10 mg to about 1000 mg of said phytoestrogenic isoflavone compound is administered to said human per day.

80. The method of claim 79 wherein between about 20 mg to about 500 mg of said phytoestrogenic isoflavone compound is administered to said human per day.

81. The method of claim 80 wherein between about 30 mg to about 300 mg of said phytoestrogenic isoflavone compound is administered to said human per day.

82. The method of claim 81 wherein between about 50 mg to about 150 mg of said phytoestrogenic isoflavone compound is administered to said human per day.

83. The method of claim 72 wherein said phytoestrogenic isoflavone compound is administered to said human in a soy protein material dietary supplement.

84. The method of claim 83 wherein said soy protein material is a phytoestrogenic isoflavone enriched material.

85. The method of claim 83 wherein said soy protein material is enriched in at least one of the aglucone isoflavones genistein, daidzein, and glycitein.

86. The method of claim 83 wherein said phytoestrogenic isoflavone compound is administered to said human in a beverage containing said soy protein material.

87. The method of claim 83 wherein said phytoestrogenic isoflavone compound is administered to said human in a food bar containing said soy protein material.

88. The method of claim 83 wherein said phytoestrogenic isoflavone compound is administered to said human in a yogurt containing said soy protein material.

89. The method of claim 72 wherein said phytoestrogenic isoflavone compound is administered to said human in a pharmaceutical composition.

90. The method of claim 89 wherein said pharmaceutical composition is a pill or a capsule containing said phytoestrogenic isoflavone compound.

* * * * *